(12) United States Patent
Olivas

(10) Patent No.: US 6,927,323 B2
(45) Date of Patent: Aug. 9, 2005

(54) LETTUCE VARIETY NAMED 'CYCLONE'

(75) Inventor: Nathan K. Olivas, Salinas, CA (US)

(73) Assignee: Progeny Advanced Genetics, Salinas, CA (US)

(*) Notice: Subject to any disclaimer, the term of this patent is extended or adjusted under 35 U.S.C. 154(b) by 174 days.

(21) Appl. No.: 10/320,656

(22) Filed: Dec. 17, 2002

(65) Prior Publication Data

US 2003/0177538 A1 Sep. 18, 2003

Related U.S. Application Data

(60) Provisional application No. 60/339,808, filed on Dec. 17, 2001.

(51) Int. Cl.$^7$ ................................................. A01H 5/00
(52) U.S. Cl. ..................................................... 800/305
(58) Field of Search ......................................... 800/305

(56) References Cited

PUBLICATIONS

USDA Plant Variety Protection Act Certificate No. 900137.*
USDA Plant Variety Protection Act Certificate No. 8800200.*

* cited by examiner

Primary Examiner—Bruce R. Campell
Assistant Examiner—S B McCormick
(74) Attorney, Agent, or Firm—Foley & Lardner, LLP

(57) ABSTRACT

This invention provides for a novel variety of Lactuca sativa variety named 'Cyclone' which is a romaine or Cos lettuce having dark green thick leaves, short compact growth, slow bolting and leaf uniformity.

5 Claims, 4 Drawing Sheets (4 of 4 Drawing Sheet(s) Filed in Color)

Cyclone

Cyclone

Cyclone Leafs

King Henry Variety      Cyclone Variety

Cyclone

US 6,927,323 B2

LETTUCE VARIETY NAMED 'CYCLONE'

BACKGROUND OF THE INVENTION

There is an ongoing need for improved lettuce varieties. Presently, there are over a thousand known lettuce cultivars within the following groups: batavia lettuce, butterhead or head lettuce, iceberg lettuce, lollo lettuce, oakleaf lettuce, and romaine or Cos lettuce.

The drawback with most presently available romaine lettuce varieties is that the outer leaves, which are much larger than the inner leaves, are either unusable or must be cut to be usable. Because the whole leaf market specifies strict leaf sizing for an acceptable product, it is desirable to have more uniform leaf size. The leaf size of typical romaine is larger than what is acceptable in the whole leaf market. Another drawback of presently available romaine lettuce varieties is that the leaves are easily damaged during harvesting and washing. Thicker leaves prevent damage that can occur during these processes.

It is the object of the invention to provide new varieties of romaine or Cos lettuce with more uniform leaf size with dark green and thick leaves.

SUMMARY OF THE INVENTION

The present invention provides a *Lactuca sativa* L. var. *longifolia* Lam plant comprising of dark green and thick leaves of uniform size. Another aspect of the present invention provides lettuce varieties with leaves approximately 15–16 cm wide and 19–20 cm long. Another aspect of the present invention provides *Latuca sativa* seed designated 'Cyclone'. Another aspect of the present invention provides a lettuce plant or its progeny obtained from the seed of 'Cyclone'. Another aspect of the invention provides for lettuce leaves obtained from 'Cyclone' and lettuce leaves from the lettuce plant or progeny from the seed of 'Cyclone'. Another aspect of the invention provides a method of making *Latuca sativa* seed by crossing 'Cyclone' as the male or female parent with *L. sativa* selection and selecting seed from the cross. Another aspect of the invention provides a method of making *L. sativa* seed by crossing two 'Cyclone' plants to produce more 'Cyclone' seeds. Another aspect of the invention provides a *Latuca sativa* plant produced from the method of crossing two 'Cyclone' plants and collecting the seeds therefrom.

During the experimental and testing stages, 'Cyclone' was designated 'PX 408'. The commercial name for the instant plant is designated the varietal name 'Cylone'.

As used herein, bolting is a condition which occurs in lettuce plants when an elongated stalk with flowers grows from within the main stem of the lettuce plant. It is the undesirable formation of flowers and seeds. Bolting destroys the flavor of the leaves by making them bitter and tough. Bolting is typically caused by exceedingly low or high temperatures, long periods of high light intensities, and drought.

As used herein, core length is the length of the internal lettuce stem; measured from the base of the cut head to the tip of the core. As used herein, core diameter is the diameter of the stem at the base of the cut head.

As used herein, heart length is the length of the dense center portion of the romaine plant. It is measured from the base of the cut stem to the first internal leaf that encloses the romaine heart.

As used herein, head length is the diameter of the vertically sliced plant, measured from the base of the cut stem to the tip of the longest outer leaf. As used herein, head length to core length is the ratio of the measured head length to the measured core length.

As used herein, frame diameter is a horizontal measurement of the plant diameter while growing, at its widest point. From outer most leaf tip to outer most leaf tip.

As used herein, head weight is the weight of the marketable plant, cut and trimmed to market specifications.

As used herein, pack out proportion is the proportion of total cartons (finished product) generated from a single tray of product.

As used herein, romaine is *Lactuca sativa* L. var. *longifolia* Lam; also known as Cos. The plant develops in an upright open or upright compact growing habit with coarse textured leafs. The leaves are longer than they are wide, cupping together to form an elongated loose head. Leaf margins are often entire or undulated, rarely frilled. Outer leafs range in color from light green to dark green with a heavy midrib. Inner heart leaves are smaller and range from light yellow to light green in color.

BRIEF DESCRIPTION OF THE DRAWINGS

The file contains at least one drawing executed in color. Copies of this patent or patent application publication with the color drawing(s) will be provided by the Office upon request and payment of the necessary fee.

DETAILED DESCRIPTION OF THE INVENTION

Figure 1:
FIG. 1 shows a whole plant, side view of the foliage of 'Cyclone', with colors being as true as possible with illustrations of this type.
Figure 2:
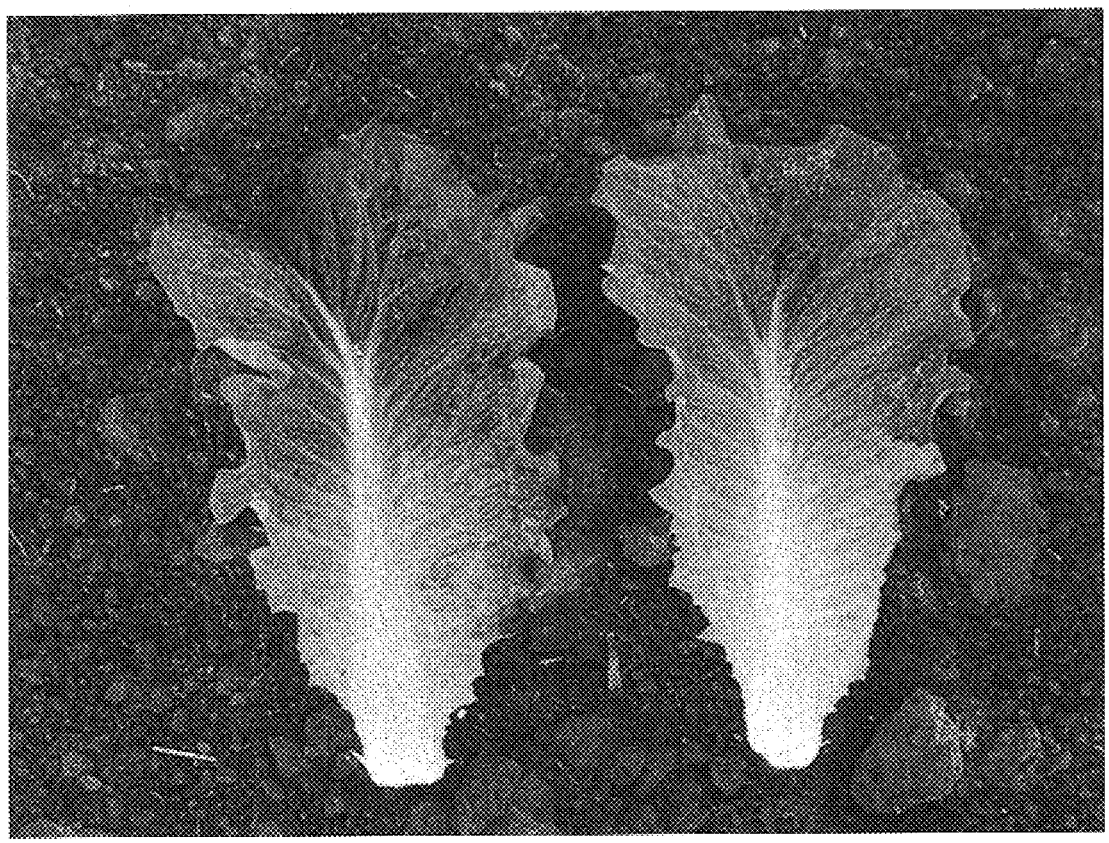
FIG. 2 shows the leaves of 'Cyclone'.
Figure 3:
FIG. 3 shows a comparison between 'Cyclone' on the right side and the variety 'King Henry' on the left side.
Figure 4:
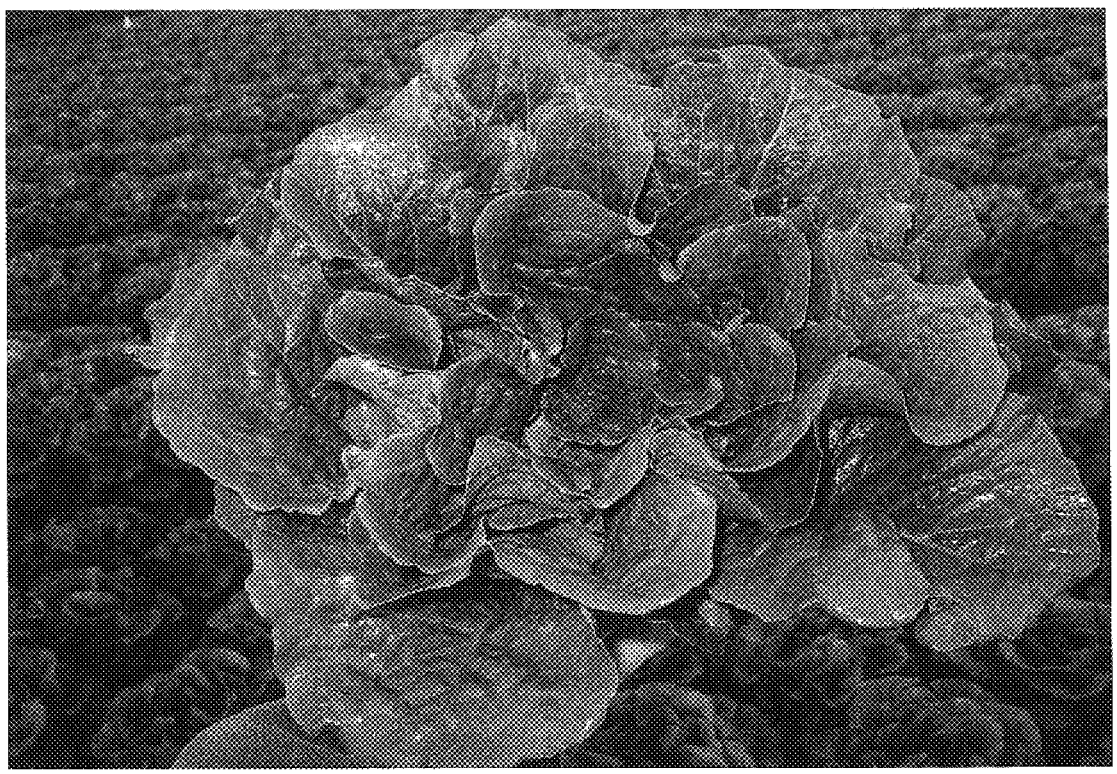
FIG. 4 shows a close-up top view of 'Cyclone'.

This invention provides novel varieties of romaine lettuce developed from a hand pollinated cross of 'Darkland' Cos (Plant Variety Protection Act Certificate No. 9000137) and 'Major' Cos (Plant Variety Protection Act Certificate No. 8800200), made in 1993 by the inventor, Nathan K. Olivas, in the San Joaquin Valley, Calif. The F1 seed harvested was designated as Gamma #035. 'Darkland' Cos, a dark green 'Parris Island' Cos type was selected as a source of dark color. 'Major' Cos was a source of weight and adaptability. The cross was made to produce a dark green, slow bolting, romaine lettuce variety.

Approximately 50 plants of the F1 seed were planted in a San Joaquin Valley production field for seed increase in 1994. The block was rogued, eliminating the self pollinating plants. The F2 seed was harvested in August 1994, labeled 94035.

Line 94035 was planted in 1996 in a San Joaquin Valley research production block. Individual plants were selected at market maturity for distinctions in type, size, color and maturity. The particular selection labeled PSR95400-47 stake # 422-1 was noted to be extremely dark in color, have an unusually thick leaf texture, and be significantly shorter and more compact than the remainder of the plants in the block. The selected plants were allowed to mature and the F3 seed from the selection was harvested individually.

The F3 seed from selection number PSR95400-47 stake #422-1 was increased in the 1997 San Joaquin Valley research production block. The block was evaluated and rogued at market maturity removing any visible off-types. The selected remaining plants exhibiting the dark color, thick leaf texture and compact growth habit were allowed to self pollinate and the F4 seed was harvested in bulk in the fall of 1997. The F4 seed was labeled SJ97-Stake #842C-W.

The F4 seed was evaluated in research and development plot trials during the 1998 growing season in the Salinas Valley of California and Yuma Ariz., where it exhibited excellent uniformity demonstrating the selected traits. Recommendation for increase was made, and the F4 seed was planted in the San Joaquin Valley Research production field in 1999. The block was planted and identified as Stake #99B1550. The line was evaluated and rogued first at market maturity, where it was noted to exhibit uniform characteristics and the desired traits. Selective rogueing was done to remove early maturing plants. The F5 seed was harvested in bulk.

The F5 line was identified as 'Cyclone' in January of 2000 and was trialed through out the Salinas Valley where it demonstrated excellent uniformity in terms of size, type and maturity. The variety, during this trialing period was identified and preliminarily tested for the whole leaf and baby leaf lettuce markets. The F5 seed was then increased in the 2000 San Joaquin Valley commercial production field as Stake #00K574. The variety was noted as uniform and stable without variants. The F6 seed was harvested in the fall of 2000.

The F6 seed was deposited with the American Type Culture Collection, P.O. Box 1549 Manassas, Va. 20108, on Dec. 12, 2001, and accorded ATCC Accession No. PTA-3922.

'Cyclone' is slow bolting. In typical summer production conditions, 'Cyclone' will bolt between 70 and 80 days from its first wet date. Bolting is a condition occurring in lettuce plants when an elongated stalk with flowers grows from within the main stem of the lettuce plant. It results in the undesirable formation of flowers and seeds. Bolting destroys the flavor of the leaves by making them bitter and tough. It is caused by exceedingly low or high temperatures, long periods of high light intensities, and drought.

The distinct characteristics of 'Cyclone' offer a significant advantage for whole leaf processing by increasing the percent recovery during the process and also offer an advantage for the baby leaf lettuce market. The leaf thickness prevents mechanical damage that can occur during the leaf removal and washing processes increasing the percentage useable product form the plant. The whole leaf market specifies strict leaf sizing for acceptable product. The leaf size of a typical romaine is larger than what is acceptable in the whole leaf market. To get leaves of acceptable sizing, the larger outer leaves and the smaller inner leaves must be discarded. Due to the short growth habit, and uniform leaf size of 'Cyclone', this variety produces a high number of leaves that fall within this specified range of acceptance. This characteristic is of economic benefit as more of the product from each plant can be processed.

EXAMPLE 1

Field Test of 'Cyclone' for Whole Leaf Market Harvested in Salinas, Calif.

Romaine produced for whole leaf processing is grown in a very similar manner as commodity romaine production. Seeds are planted at 2 inch spacing, with 2 seed lines on each raised bed. The beds are on 38 to 42 inch centers depending on growing location and cultural practices. In some circumstances wider beds, with 80 inch centers are used, and 5 to 6 seed lines will be planted on each. When the plants have grown to approximately their $4^{th}$ leaf stage, the crop is thinned, generally creating 7–12 inches of space between the plants on a seed line. Romaine grown for the whole leaf process is typically grown at 10 inch spacing. At maturity the plants are harvested slightly less mature than typical commodity romaine, and packed in plastic bins, rather than the commercial cardboard boxes. Ideal weights for the whole leaf pack is about 30 pounds per bin of 24 plants, versus 35 to 42 pounds for the commodity market. Heavier weights are acceptable but cause for increased culling due to more variable leaf size and increased leaf damage incurred in the tighter packing. The variety tested extremely well, producing plants with thick heavy leaves that were uniform in size, shape and color.

Description of Field Evaluation

Trials of Cyclone, Major Cos, and Darkland Cos were planted in commercial fields of romaine lettuce, and grown with the exact same treatment as the commercial variety. At the time of ideal harvest the trial was evaluated. A minimum of 12 plants from each variety were evaluated. First, the frame diameters of 12 plants were measured to the nearest centimeter, at their widest point. A minimum of 12 plants of each variety were then cut and trimmed to market specifications. The core diameters were measured and recorded to the nearest millimeter at the base of the cut plant. The plants were then weighed individually to the nearest gram and the weights recorded. Each plant was then sliced vertically. The core lengths were measured to the nearest millimeter, from the base of the cut stem, to the tip of the growing point, and recorded. The heart length was then measured to the nearest millimeter from the base of the cut stem to the tip of the outer most heart leaf. The heart lengths were recorded. The head length was then measured from the base of the cut stem to the outer most leaf tip. These measurements were recorded to the nearest millimeter.

An additional 12 plants were cut and trimmed to market specifications. The leaves of each plant were removed and counted. The leaf counts were recorded and averaged. The removed leaves were then measured for length, width and thickness. The length was measured to the nearest millimeter from the base of the petiole to the tip of the leaf. The diameter was measured at the widest point of the leaf to the nearest millimeter. A caliper was then used to measure the leaf thickness (depth). The leaf thickness was measured in from the leaf margin one third of the way down from the leaf tip. Only leaf tissue was measured, leaf veins and the mid rib were avoided.

Description of Measurements

The romaine plant is cut according to fresh market standards, at market maturity. The plant is weighed, the core diameter is measured, and then the plant is sliced vertically. The romaine heart is defined as the part of the plant enclosed by the outer most cupping leaf. This area is the densest part of the plant and the color varies from white to yellow to light green as the leaves mature. For our evaluation purposes, the heart length is measured from the base of the cut plant stem (core) to the tip of the outer most cupping leaf that forms the heart.

The stem length is measured from the base of the cut stem to the stem tip, at market maturity. Head height is measured vertically from the base of the cut stem to the tip of the margin of the longest leaf. Plant height is the total plant height of the growing plant from the top of the bed to the highest part of the plant. Head height is a measurement of the plant height once cut to market standards.

The colors were measured using the Munsell Color Chart for Plant Tissues.

Tables 1–6 show field test data for 'Cyclone' for the whole leaf market and were harvested Jun. 27, 2001 in Salinas, Calif.

Table 1 is a comparison between 'Cyclone' and 'Darkland' Cos with respect to core diameter, core length, and heart length.

TABLE 1

|  | Core Diameter (mm) | | Core Length (mm) | | Heart Length (mm) | |
| --- | --- | --- | --- | --- | --- | --- |
|  | 'Cyclone' | 'Darkland' Cos | 'Cyclone' | 'Darkland' Cos | 'Cyclone' | 'Darkland' Cos |
| Average | 39.9 | 42.1 | 45.8 | 52.8 | 182.5 | 207.5 |
| Stan dev | 1.83E+00 | 2.02E+00 | 6.15E+00 | 7.78E+00 | 1.71E+01 | 1.60E+01 |
| T test | 1.16E−02 | | 2.29E−02 | | 1.27E−03 | |

Table 2 is a comparison between 'Cyclone' and 'Darkland' Cos with respect to head length, core length, frame diameter and head weight.

TABLE 2

|  | Head length (mm) | | Core Length (cm) | | Frame diameter (cm) | | Head wt. (g) | |
| --- | --- | --- | --- | --- | --- | --- | --- | --- |
|  | 'Cyclone' | 'Darkland' Cos | 'Cyclone' | 'Darkland' Cos | 'Cyclone' | 'Darkland' Cos | 'Cyclone' | 'Darkland' Cos |
| Average | 229.2 | 285.0 | 5.0 | 5.5 | 31.0 | 38.1 | 697.3 | 896.5 |
| Stan dev | 1.88E+01 | 1.73E+01 | 3.75E−01 | 7.78E−01 | 1.95E+00 | 1.73E+00 | 1.30E+02 | 1.45E+02 |
| T test | 1.48E−07 | | 8.48E−02 | | 3.66E−09 | | 1.82E−03 | |

Table 3 is a comparison between 'Cyclone' and 'Darkland' Cos with respect to leaf count, leaf length and leaf width.

TABLE 3

|  | Leaf Count/Plant | | Leaf Length | | Leaf Width | |
| --- | --- | --- | --- | --- | --- | --- |
|  | 'Darkland' Cos | 'Cyclone' | 'Darkland' Cos | 'Cyclone' | 'Darkland' Cos | 'Cyclone' |
| Average | 21 | 21 | 26 | 19 | 16 | 15 |
| Standard Dev | 1.215431087 | 2.79067712 | 3.670651742 | 1.801558779 | 3.300318964 | 2.010207868 |
| T-Test | 0.925301893 | | 4.42705E−08 | | 0.638773373 | |

Table 4 is a comparison between 'Cyclone' and 'Major' Cos with respect to core diameter, core length and hearth length.

TABLE 4

|  | Core Diameter (mm) | | Core Length (mm) | | Heart Length (mm) | |
| --- | --- | --- | --- | --- | --- | --- |
|  | 'Cyclone' | 'Major' Cos | 'Cyclone' | 'Major' Cos | 'Cyclone' | 'Major' Cos |
| Average | 39.9 | 42.8 | 47.0 | 42.8 | 182.5 | 225.0 |
| Stan dev | 1.83E+00 | 3.72E+00 | 7.29E+00 | 3.72E+00 | 1.71E+01 | 2.39E+01 |
| T test | 2.72E−02 | | 8.47E−03 | | 5.23E−05 | |

Table 5 is a comparison between 'Cyclone' and 'Major' Cos of head length, core length, frame diameter, and head weight.

TABLE 5

|  | Head length (mm) | | Core Length | | Frame diam (cm) | | Head wt. (g) | |
| --- | --- | --- | --- | --- | --- | --- | --- | --- |
|  | 'Cyclone' | 'Major' Cos | 'Cyclone' | 'Major' Cos | 'Cyclone' | 'Major' Cos | 'Cyclone' | 'Major' Cos |
| Average | 229.2 | 298.3 | 4.7 | 7.0 | 31.0 | 39.1 | 697.3 | 630.8 |
| Stan dev | 1.88E+01 | 1.75E+01 | 1.00E+00 | 6.86E−01 | 1.95E+00 | 1.44E+00 | 1.30E+02 | 1.13E+02 |
| T test | 4.22E−09 | | 1.56E−06 | | 8.58E−11 | | 1.95E−01 | |

Table 6 is a comparison between 'Cyclone' and 'Major' Cos with respect to leaf count, leaf length and leaf width.

TABLE 6

|  | Leaf Count | | Leaf Length | | Leaf Width | |
| --- | --- | --- | --- | --- | --- | --- |
|  | 'Major' Cos | 'Cyclone' | 'Major' Cos | 'Cyclone' | 'Major' Cos | 'Cyclone' |
| Average | 20 | 21 | 26 | 19 | 17 | 16 |
| Standard Dev | 0.88762536 | 2.79067712 | 4.87204701 | 1.755442664 | 4.070432539 | 2.03650888 |
| T-Test | 0.56024213 | | 1.9318E−05 | | 0.334247376 | |

Tables 7–12 show field test data for 'Cyclone' for the whole leaf market that were harvested Aug. 24, 2001 in Salinas, Calif.

Table 7 is a comparison between 'Cyclone' and 'Darkland' Cos with respect to core diameter, core length and heart length.

TABLE 7

|  | Core Diameter (mm) | | Core Length (mm) | | Heart Length (mm) | |
| --- | --- | --- | --- | --- | --- | --- |
|  | 'Darkland' Cos | 'Cyclone' | 'Darkland' Cos | 'Cyclone' | 'Darkland' Cos | 'Cyclone' |
| Average | 35.2 | 36.2 | 41.3 | 39.0 | 235.0 | 220.8 |
| Stan dev | 3.27E+00 | 1.64E+00 | 4.77E+00 | 4.07E+00 | 2.24E+01 | 1.16E+01 |
| T test | 3.54E−01 | | 2.27E−01 | | 6.45E−02 | |

Table 8 is a comparison between 'Cyclone' and 'Darkland' Cos of head length, core length, frame diameter, and head weight.

TABLE 8

|  | Head length (mm) | | Core Length (cm) | | Frame diameter (cm) | | Head wt. (g) | |
| --- | --- | --- | --- | --- | --- | --- | --- | --- |
|  | 'Darkland' Cos | 'Cyclone' | 'Darkland' Cos | 'Cyclone' | 'Darkland' Cos | 'Cyclone' | 'Darkland' Cos | 'Cyclone' |
| Average | 290.8 | 272.5 | 7.1 | 7.1 | 38.0 | 34.8 | 515.7 | 476.3 |
| Stan dev | 2.35E+01 | 9.65E+00 | 7.00E−01 | 6.79E−01 | 1.21E+00 | 1.11E+00 | 1.09E+02 | 3.81E+01 |
| T test | 2.05E−02 | | 8.51E−01 | | 1.03E−06 | | 2.50E−01 | |

Table 9 is a comparison between 'Cyclone' and 'Darkland' Cos with respect to leaf count, leaf length and leaf width.

TABLE 9

|  | Leaf Count/Plant | | Leaf Length (cm) | | Leaf Width (cm) | |
| --- | --- | --- | --- | --- | --- | --- |
|  | 'Cyclone' | 'Darkland' Cos | 'Cyclone' | 'Darkland' Cos | 'Cyclone' | 'Darkland' Cos |
| Average | 19 | 18 | 20 | 26 | 16 | 16 |
| Standard Dev | 1.53741223 | 1.90692518 | 1.66315419 | 3.166897499 | 2.064741605 | 3.314861 |
| T-Test | 0.171295953 | | 5.8898E−08 | | 0.683826647 | |

Table 10 is a comparison between 'Cyclone' and 'Major' Cos with respect to core diameter, core length and heart length.

TABLE 10

|  | Core Diameter (mm) | | Core Length (mm) | | Heart Length (mm) | |
| --- | --- | --- | --- | --- | --- | --- |
|  | 'Major' Cos | 'Cyclone' | 'Major' Cos | 'Cyclone' | 'Major' Cos | 'Cyclone' |
| Average | 40.0 | 36.2 | 46.1 | 39.0 | 264.2 | 220.8 |
| Stan dev | 1.13E+00 | 1.64E+00 | 6.73E+00 | 4.07E+00 | 1.56E+01 | 1.16E+01 |
| T test | 1.06E−06 | | 5.00E−03 | | 1.11E−07 | |

Table 11 is a comparison between 'Cyclone' and 'Major' Cos with respect to head length, core length, frame diameter, and head weight.

TABLE 11

|  | Head length (mm) | | Core Length (cm) | | Frame diameter (cm) | | Head wt. (g) | |
| --- | --- | --- | --- | --- | --- | --- | --- | --- |
|  | 'Major' Cos | 'Cyclone' | 'Major' Cos | 'Cyclone' | 'Major' Cos | 'Cyclone' | 'Major' Cos | 'Cyclone' |
| Average | 333.3 | 272.5 | 7.3 | 7.1 | 39.9 | 34.8 | 645.8 | 476.3 |
| Stan dev | 1.43E+01 | 9.65E+00 | 9.38E−01 | 6.79E−01 | 2.71E+00 | 1.11E+00 | 6.73E+01 | 3.81E+01 |
| T test | 2.78E−11 | | 3.80E−01 | | 4.81E−06 | | 1.39E−07 | |

Table 12 is a comparison between 'Cyclone' and 'Major' Cos with respect to leaf count, leaf length and leaf width.

TABLE 12

|  | Leaf Count/Plant | | Leaf Length (cm) | | Leaf Width (cm) | |
| --- | --- | --- | --- | --- | --- | --- |
|  | 'Major' Cos | 'Cyclone' | 'Major' Cos | 'Cyclone' | 'Major' Cos | 'Cyclone' |
| Average | 20 | 19 | 26 | 20 | 16 | 16 |
| Standard Dev | 2.50302847 | 1.53741223 | 3.34191877 | 1.637552731 | 3.375998878 | 2.01246118 |
| T-Test | 0.21472583 | | 3.8314E−08 | | 0.735138583 | |

Tables 13–17 contain field test data for 'Cyclone' for the whole leaf market that were harvested Mar. 10, 2002 in Salinas, Calif.

Table 13 is a comparison between 'Cyclone' and 'Darkland' Cos with respect to core diameter, core length and heart length.

TABLE 13

|  | Core Diameter (mm) | | Core Length (mm) | | Heart Length (mm) | |
| --- | --- | --- | --- | --- | --- | --- |
|  | 'Darkland' Cos | 'Cyclone' | 'Darkland' Cos | 'Cyclone' | 'Darkland' Cos | 'Cyclone' |
| Average | 40.3 | 38.4 | 53.3 | 51.3 | 168.6 | 176.7 |
| Stan dev | 2.99E+00 | 3.55E+00 | 6.76E+00 | 8.25E+00 | 1.01E+01 | 1.39E+01 |
| T test | 1.85E−01 | | 5.23E−01 | | 1.17E−01 | |

Table 14 is a comparison between 'Cyclone' and 'Darkland' Cos with respect to head length, core length, frame diameter, and head weight.

TABLE 14

|  | Head length (mm) | | Core Length (cm) | | Frame diameter (cm) | | Head wt. (g) | |
| --- | --- | --- | --- | --- | --- | --- | --- | --- |
|  | 'Darkland' Cos | 'Cyclone' | 'Darkland' Cos | 'Cyclone' | 'Darkland' Cos | 'Cyclone' | 'Darkland' Cos | 'Cyclone' |
| Average | 273.1 | 242.0 | 5.2 | 4.8 | 36.8 | 33.7 | 1132.2 | 994.6 |
| Stan dev | 2.37E+01 | 1.81E+01 | 7.18E−01 | 6.83E−01 | 1.27E+00 | 1.67E+00 | 2.26E+02 | 1.44E+02 |
| T test | 1.54E−03 | | 1.91E−01 | | 3.00E−05 | | 8.97E−02 | |

Table 15 is a comparison between 'Cyclone' and 'Darkland' Cos with respect to leaf count, leaf length and leaf width.

TABLE 15

|  | Leaf Count/Plant | | Leaf Length (mm) | | Leaf Width (mm) | |
| --- | --- | --- | --- | --- | --- | --- |
|  | 'Darkland' Cos | 'Cyclone' | 'Darkland' Cos | 'Cyclone' | 'Darkland' Cos | 'Cyclone' |
| Average | 36 | 31 | 250 | 225 | 161 | 162 |
| Standard Dev | 3.01511345 | 3.77692355 | 21.5100955 | 10.88166009 | 14.23709018 | 18.9222787 |
| T-Test | 3.38E−03 | | 5.13E−05 | | 8.96E−01 | |

Table 16 is a comparison between 'Cyclone' and 'Darkland' Cos with respect to leaf depth.

TABLE 16

|  | Leaf Depth (mm) | |
| --- | --- | --- |
|  | 'Darkland' Cos | 'Cyclone' |
| Average | .545 | .63 |
| Standard Dev | 0.1145931 | 0.13018206 |
| T-Test | 3.46E−02 | |

Table 17 is a comparison between 'Cyclone' and 'Darkland' Cos with respect to days to maturity and color.

TABLE 17

|  | Date Mature | Days to Maturity | Color |
| --- | --- | --- | --- |
| 'Cyclone' | Jun. 7, 2002 | 89 | 7.5gy4/4 |
| 'Darkland' Cos | Jun. 3, 2002 | 85 | 5gy5/6 |

Table 18 is a whole leaf process data comparison between 'Cyclone' and the commercial Cos variety 'Frontier' of the pack out proportion. The pack out number is the proportion of total cartons (finished product) generated from a single tray of product. All trays contain 24 harvested romaine plants. All finished cartons are 10 pounds of processed and stacked whole leaves of romaine, all of which meet a specific size requirement. Based on the comparison data in Table 18, 'Cyclone' is statistically higher yielding.

TABLE 18

| | Trays Processed | | Total Cartons | | Pack out percentage (%) | |
|---|---|---|---|---|---|---|
| | 'Cyclone' | 'Frontier' | 'Cyclone' | 'Frontier' | 'Cyclone' | 'Frontier' |
| Average | 755.4 | 836.2 | 915.6 | 869.8 | 1.272 | 1.048 |
| Standard Dev | 2.67E+02 | 1.90E+02 | 2.09E+02 | 1.66E+02 | 2.44E−01 | 1.02E−01 |
| T-Test | 5.96E−01 | | 7.11E−01 | | 4.63E−02 | |

EXAMPLE 2

Field Test of 'Cyclone' for Baby Leaf Market

Baby leaf lettuce production can also be described as 'spring mix' or 'salad mix'. The romaine is sewn at a much higher seed rate, and is typically planted raw or in a much smaller or lighter pelletting material. Seed rates start at a minimum of 1.5 million seeds per acre and can go as high as 2.5 million depending on cultural practices. This is compared to an average seeding rate of about 160,000 seeds per acre in commodity romaine production. Typically baby leaf production is done on raised beds with 80 inch centers, with 16 to 24 seed lines per bed. The crop is not thinned, and typically harvested when the plants have between 4 and 7 leaves ranging in leaf length from 3 to 5 inches. The romaine lettuce is generally part of a mix of lettuce types that vary in color, taste and texture. Multiple romaine types may be used in the process to provide differences in color and texture.

I claim:

1. A *Lactuca sativa* seed having ATCC patent deposit accession No. PTA-3922.

2. A lettuce plant designated 'Cyclone', obtained from the seed of claim 1.

3. Lettuce leaves obtained from the plant of claim 2.

4. A method of making *Lactuca sativa* seeds comprised of crossing the plant of claim 2 with another *L. sativa* plant selection and harvesting seed therefrom.

5. A method of making *L. sativa* variety 'Cyclone' by selecting seeds from the cross of one 'Cyclone' plant with another 'Cyclone' plants.

* * * * *